United States Patent [19]
Jones et al.

[11] Patent Number: 5,482,714
[45] Date of Patent: Jan. 9, 1996

[54] WATER IMPERMEABLE SKIN PROTECTANT BASED UPON REVERSE WATER EMULSION

[75] Inventors: David P. Jones; William H. Woller, both of San Antonio, Tex.

[73] Assignee: Healthpoint Medical Limited Partnership, Reno, Nev.

[21] Appl. No.: 272,422

[22] Filed: Jul. 8, 1994

[51] Int. Cl.⁶ ..................................................... A61K 7/46
[52] U.S. Cl. ............................................................ 424/401
[58] Field of Search ................................................ 424/401

[56] References Cited

FOREIGN PATENT DOCUMENTS 222580   5/2087   European Pat. Off. .

*Primary Examiner*— Paul J. Killos
*Attorney, Agent, or Firm*—Zarley, McKee, Thomte, Voorhees & Sease

[57] ABSTRACT

A water impermeable skin protectant which is an emulsified ointment based upon a reverse water emulsion. It provides a substantially waterproof external phase and substantially water soluble internal phase. This is accomplished by a combination of a Cyclomethicone lipogel blend and a silicone water in oil emulsifier, preferably in combination with minors to enhance elegance, preservative and a stabilizer.

12 Claims, No Drawings

WATER IMPERMEABLE SKIN PROTECTANT BASED UPON REVERSE WATER EMULSION

BACKGROUND OF THE INVENTION

This invention relates to a skin protectant, usually for use after skin cleansing. It is a protectant that is especially designed for irritated or compromised skin.

Ointments to be used on irritated skin in order to eliminate the pain and irritating feeling are known. Many are petrolatum based and contain a zinc oxide pigment in order to enhance wound healing.

A significant problem in use of the presently available skin protectants, which are petrolatum based and contain zinc oxide, is that they in fact do not ideally protect compromised areas. Moreover, the presence of zinc oxide often compounds the problem of difficulty of removal during wound cleansing. Put another way, because the zinc oxide is somewhat difficult to remove, a nurse applicator is apt to over scrub in cleansing. As a result, skin irritation is exacerbated, skin may be compromised or torn, and the ultimate healing process delayed.

Problems such as those above described are very common in association with chronic diarrhea, enzymatic drainage, or incontinence. For use in conjunction with these three problems particularly, a skin protectant needs to be one which is preferably greaseless, one which provides a good moisture barrier, and one with excellent adhesion to both moist and dry skin.

To accomplish some of the earlier mentioned attributes, some skin ointments are oil based gels. Some of these have even developed into clear oil based gels so that the underlying wound can be seen. Oil based gels do provide maximized protection of the underlying skin. However, this is provided at some sacrifice. The sacrifice is that while they are excellent protectants, they are often difficult to remove, and during the removal process may in fact adhere to the compromised skin and in turn exacerbate the irritation. This, of course, is an effect exactly the opposite of what is needed for a good protectant.

In an effort to overcome some of the problems of oil based ointment protectants as used for compromised skin, some have worked with water based protectant systems. While these are easier to apply, they do not have a good skin feel and usually sacrifice full protection from irritation by feces and urine.

It therefore can be seen that in the art as developed there is a balancing or tradeoff effect between normally used skin protectant ointments that are oil based and normally used skin protectants that are water based. Each has its own inherent advantages and its own inherent disadvantages. Thus as can be seen, there is a continuing need for new skin protectants especially adapted for compromised skin such as accompanies chronic diarrhea, enzymatic drainage, or incontinence.

It now has been discovered that a preparation which provides co-action between its ingredients to provide a water impermeable skin protectant based upon a reverse water emulsion will function to provide a product which has the best advantages of both an oil base and a water base. The advantages of the oil based product are provided on the outside surface of the product and at the same time provide an interior surface that is substantially a water soluble phase. As a result, the exterior phase adequately protects, and the interior allows the skin to breathe. At the same time the preparation can be washed away without significant damage to the skin via abrasion.

It is therefore a primary objective of this invention to provide a combination of ingredients which co-act to provide the above substantially improved skin protectant which for the first time provides for advantages of oil phase and water phase, both in the same composition.

Another objective of the present invention is to provide a skin ointment formulation which is based upon water, but is at the same time substantially waterproof.

Another objective of the present invention is to provide a water based product that provides skin protection and provides a substantial surface barrier against water invasion of the underlying wound.

Another objective of the present invention is to provide a skin protectant of water base that still has an elegant feel and still the proper drag so that it will be readily accepted by nurse applicators and not uncomfortable to the patient.

A yet further objective of the present invention is to provide a skin protectant which adheres to compromised skin, especially that compromised by incontinence, and which provides moisture to the skin and yet provides an adequate barrier to permeation, and which can be easily removed during wound cleansing, without compromising or tearing the skin.

A yet further objective of the present invention is to provide a skin protectant which is stable, easy to formulate, and suitable for tubular dispensers.

The method and manner of accomplishing each of the above objectives as well as others will become apparent from the detailed description of the invention which follows.

SUMMARY OF THE INVENTION

A water impermeable skin protectant based upon a reverse water emulsion. The emulsified ointment comprises a combination of a lipogel blend that is a mixture of cyclomethicone and aluminum-magnesium-hydroxy-stearate with an emulsifying agent for reverse emulsification. This provides an ointment emulsion that is oil phase on the external phase and water phase on the internal phase of the emulsion. Minors are added to enhance elegance, and for preservation and stabilization of the emulsified ointment. The emulsifying agent is preferably a polysiloxane polyalkylene polyether copolymer.

DETAILED DESCRIPTION OF THE INVENTION

One major component of the composition necessary to achieve the water impermeable characteristic of this invention is a lipogel blend. The term "lipogel" as used herein refers to a composition that is lipophilic in nature and can function in combination with a gelling agent as a rheological modifier for ointment compositions.

A suitable lipogel agent for use herein which meets these criteria is a composition sold by Giulini Corporation, 105 East Union Avenue, Bound Brook, N.J. under the trademark Gilugel SIL 5®. This composition is a cyclomethicone pentamer (and) an aluminum-magnesium-hydroxy-stearate. It has the following chemical structure:

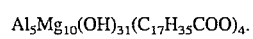

$$Al_5Mg_{10}(OH)_{31}(C_{17}H_{35}COO)_4.$$

This material is derived from aluminum-magnesium-hydroxy-sulfate, a well-known pharmaceutical active ingredient used in antacids for the treatment of gastrointestinal ulcers and hyperchlorhydria. The compounds are characterized by a multi-layer lattice structure of positively charged octahedral layers of $[Al_5Mg_{10}(OH)_{30}]^{5+}$ and negatively charged intermediary layers of $[(SO_4)_2OH \times H_2O]^{5-}$. If the intermediary sulfate ions are replaced with stearate anions, the resulting structure, aluminum-magnesium-hydroxystearate, is made hydrophobic. This material may serve as an excellent gelling agent for a wide range of cosmetic oils. Gilugel Sil 5® is a lipogel composed of 75% Cyclomethicone pentamer and 25% aluminum-magnesium-hydroxystearate. Here it is used as a total or partial replacement for the normal use of oils, fatty alcohols, waxes or gelling agents in skin protectants. It controls viscosity, enhances thermal stability at extreme temperatures (5° C.–50° C.) and improves the suspension of insoluble materials. The chemical and physical properties of this composition are the following:

| Colour and form | white pasty gel |
| --- | --- |
| Specific gravity [g × ml⁻¹] | 0.94–0.98 |
| Moisture content [%] | 0.1–0.4 |
| Micropenetration [1/10 mm] | |
| at 20° C. | 41 |
| at 40° C. | 53 |
| $Al_2O_3$ [%] | 1.4–2.6 |
| MgO [%] | 2.9–4.6 |
| Fatty acid content [%] | 7.4–11.2 |
| Heavy metals [ppm] | max. 30 |

The above lipogel blend, or blends of from 50:50 to 75:25 are used in the composition of the present invention at a range of from about 10% to about 25% of the total composition on a weight basis, but preferably at about 12% to about 20% by weight of the composition. Generally, for final compositions that comprise from about 10% to about 25% of the lipogel blend, the amount of the reverse emulsifying agent should be within the range of from about 2% to about 8% and preferably from about 4% to about 6% of the total composition. Suitable reverse emulsifying agents are water in oil emulsifiers. Such can be and are preferably polysiloxane polyalkylene polyether copolymers combined with non-ionic organic emulsifiers. These have the chemical structure of:

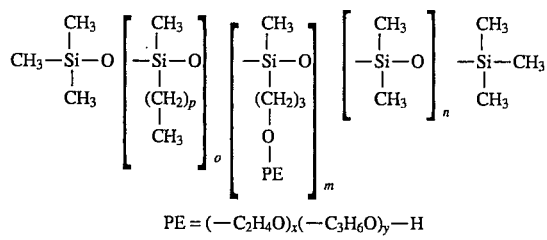

$$PE = (-C_2H_4O)_x(-C_3H_6O)_y-H$$

This may generally be described chemically as above described and may also at times be referred to as Cetyl Dimethicone Copolyol (and) Polyglyceryl-4-isostearate (and) Hexyl Laurate.

When the above reverse emulsifier and lipogel blend is used, the reverse emulsion formed with water is distinguished by its very high tolerance towards heat and freezing.

The composition should contain from 5% to 30% by weight, preferably from 5% to 15% by weight of cyclomethicone. This is commercially available from Dow Corning and in the present composition functions to enhance spreading, lubricity, and dry feel to provide less tackiness and less of a greasy feel.

For the composition of the present invention to be stable, it is also necessary that an electrolyte be added. Generally, the electrolyte acts as a stabilizing agent for the reverse emulsion. Suitable electrolytes are chlorides of alkali and alkaline earth materials. Sodium chloride is a preferred stabilizer. The amount of electrolyte added will vary from about 1.0% by weight to about 3.0% by weight, preferably from about 1.5% by weight to about 2.5% by weight, and most preferably from about 1.8% by weight to about 2.2% by weight. When the above composition with these four co-acting ingredients, lipogel blend, the reverse emulsifying agent, cyclomethicone and the stabilizing electrolyte are used in a water base (purified water), this composition provides the basic ointment formulation.

As those skilled in the art know, minors to enhance elegance, preserve and to stabilize may be added. Typical preservatives such as imidurea can be added at within the range of 0.05% to 2.0%, preferably 0.1% to about 0.5%. Imidurea is not the only preservative that may be used, and others include: methyl paraben, phenoxy ethanol, diazolidinyl urea, DMDM hydantoin, benzyl alcohol.

The balance of the system can be minors and can vary, but generally suitable minors would include agents to provide an increased level of waterproofing. Suitable ingredients that may do this are commercially available silicones (dimethicone) at a weight level of from about 1% to about 30%, preferably from about 1% to about 15%, and more normally from about 1% to about 5%. Dimethicone is the preferred compound.

Non-volatile polyalkylsiloxanes include, for example, polydimethylsiloxanes (Dimethicone) with viscosities ranging from about 5–1000 centistokes (cs) at 25° C. These siloxanes are available, for example, from the General Electric Company as the VISCASIL series and from Dow Corning as the Dow Corning 200 and 225 products. Preferably, the viscosity of these siloxanes selected have a viscosity of about 10 to about 500 cs, and most preferably, a viscosity of up to about 350 cs.

The amount of water for the ointment base, especially for incontinence compromised skin, should be from about 50% to about 80%, and most preferably from about 60% to about 75%. Moreover, the oil phase is on the external phase, and the water phase is on the internal phase of the emulsion. As a result, the composition provides an effective barrier between the atmosphere and the skin, yet provides a cosmetically elegant preparation. This has several important advantages. In the first instance, the wound can be easily cleansed without significant abrasion of the compromised skin. As a result, little damage occurs to the skin and the patient feels less pain. At the same time, advantages of effective protection normally associated only with oil bases occur since the emulsion is oil phase on the exterior surface. Therefore, as a result of this unique combination, the skin is effectively shielded from harsh cleansers, powders, irritation from feces and urine, and yet the product does not provide a greasy feel. Moreover, it can be readily cleansed.

The following examples are offered to further illustrate, but not limit the process of the present invention.

EXAMPLE

A cream composition of the present invention was prepared having the following formula:

| COMPONENT | % W/W | AMOUNT |
| --- | --- | --- |
| Purified Water USP | 67.9 | 407 L/Kg |
| Sodium Chloride | 2.00 | 12.0 Kg |
| Imidurea | 0.100 | 600 gm |
| Cyclomethicone | 9.00 | 54000 gm |
| Dimethicone | 1.00 | 6000 gm |
| Cyclomethicone (and) Aluminum/ Magnesium Hydroxide Stearate | 15.0 | 90000 gm |
| Cetyl Dimethicone Copolyol (and) Polyglyceryl-4-Isostearate (and) Hexyl Laurate | 5.00 | 30000 gm |

The lipid materials were blended, and the water, imidurea and sodium chloride were mixed to provide a water phase. The lipids and water phase were then mixed and blended in a high shear mixer until homogeneous. The resulting composition was noted to be an excellent protectant, generally waterproof, had a pleasant feel, and yet could be washed without extreme skin pressure. Water droplets were suspended in the oil base, and when they evaporated the composition was noted to leave a continuous film of protection that lasted much longer than typical oil in water emulsions.

What is claimed is:

1. A water impermeable skin protectant based upon a reverse water emulsion that provides substantial waterproofing of the skin, comprising:

from about 10% to about 25% of a lipogel blend that is a mixture of cyclomethicone and aluminum-magnesium-hydroxy-stearate;

from about 2% to about 8% of a reverse emulsifying agent which will provide an ointment emulsion that is oil phase on the exterior surface and water phase on the interior surface;

from about 5% to 30% of cyclomethicone;

from about 1.0% to about 3.0% by weight of stabilizing inorganic electrolyte; and water and minors.

2. The composition of claim 1 which comprises from about 12% to about 20% of the lipogel blend.

3. The composition of claim 1 which comprises from about 4% to about 6% of the reverse emulsifying agent.

4. The composition of claim 1 which comprises from about 5% to about 15% of cyclomethicone.

5. The composition of claim 1 which has as minors an elegance enhancer, a preservative, and a waterproofing agent.

6. The composition of claim 1 which comprises by weight from about 50% to about 80% USP purified water.

7. The composition of claim 6 which comprises from about 60% by weight to about 75% by weight purified USP water.

8. The composition of claim 1 which is packaged in a tubular dispenser.

9. The composition of claim 1 wherein the lipogel blend is cyclomethicone pentamer and aluminum-magnesium-hydroxy-stearate.

10. The composition of claim 9 wherein the composition of said lipogel blend is 75% cyclomethicone pentamer and 25% aluminum-magnesium-hydroxy-stearate.

11. The composition of claim 1 wherein the reverse emulsifying agent is Cetyl Dimethicone Copolyol, Polyglyceryl-4-isostearate, and Hexyl Laurate.

12. The composition of claim 1 wherein the stabilizing inorganic electrolyte is sodium chloride.

* * * * *